(12) United States Patent
Lin et al.

(10) Patent No.: US 11,833,241 B2
(45) Date of Patent: Dec. 5, 2023

(54) METHOD FOR ENHANCING SKIN MOISTURE WITH WHITE ROSELLE EXTRACT

(71) Applicant: TCI CO., LTD., Taipei (TW)

(72) Inventors: Yung-Hsiang Lin, Taipei (TW); Margaret Lai, Taipei (TW); Yin-Di Su, Taipei (TW)

(73) Assignee: TCI CO., LTD., Taipei (TW)

( * ) Notice: Subject to any disclaimer, the term of this patent is extended or adjusted under 35 U.S.C. 154(b) by 34 days.

(21) Appl. No.: 17/586,811

(22) Filed: Jan. 28, 2022

(65) Prior Publication Data

US 2022/0241182 A1 Aug. 4, 2022

Related U.S. Application Data

(60) Provisional application No. 63/143,971, filed on Feb. 1, 2021.

(51) Int. Cl.
| | | |
|---|---|---|
| *A61K 36/00* | (2006.01) | |
| *A61K 8/9789* | (2017.01) | |
| *A23L 33/105* | (2016.01) | |
| *A61Q 19/00* | (2006.01) | |

(52) U.S. Cl.
CPC .......... *A61K 8/9789* (2017.08); *A23L 33/105* (2016.08); *A61Q 19/00* (2013.01)

(58) Field of Classification Search
None
See application file for complete search history.

(56) References Cited

FOREIGN PATENT DOCUMENTS

WO 2022003056 A1 1/2022

OTHER PUBLICATIONS

Revilla et al. (1998) J. Agric. Food Chem. 46: 4592-4597. (Year: 1998).*
Raskin et al. (2004) Current Pharmaceutical Design 10, 3419-3429. (Year: 2004).*
EESR dated Jul. 22, 2022, listed in related European patent application No. 22 154 105.5 (publication No. EP4046624).
Examination report dated Jul. 25, 2023, listed in correspondent Taiwan patent application No. 22154105.5 (Publication No. 4046624).
An Insight into Simulated Product Development: Hibiscus Tea, Dr. Jyoti D. Vora et al., IOSR Journal of Biotechnology and Biochemistry, Apr. 30, 2016 (Apr. 30, 2016), pp. 36-44, XP93065837 https://www.iosrjournals.org/iosr-jbb/papers/Vol2-issue3/H02033644.pdf.

* cited by examiner

*Primary Examiner* — Russell G Fiebig
(74) *Attorney, Agent, or Firm* — Chieh-Mei Wang

(57) ABSTRACT

A method for enhancing skin moisture of a subject in need thereof includes administering to the subject a composition including a white roselle (*Hibiscus sabdariffa* cv.) extract. The white roselle extract is obtained by lysing a cell wall of a white roselle calyx by ice crystals and extracting the lysed white roselle calyx with a solvent.

10 Claims, 6 Drawing Sheets

Specification includes a Sequence Listing.

METHOD FOR ENHANCING SKIN MOISTURE WITH WHITE ROSELLE EXTRACT

CROSS-REFERENCE TO RELATED APPLICATION

This application claims the benefit of U.S. provisional application Ser. No. 63/143,971, filed on Feb. 1, 2021. The entirety of the above-mentioned patent application is hereby incorporated by reference herein and made a part of the specification.

REFERENCE OF AN ELECTRONIC SEQUENCE LISTING

The contents of the electronic sequence listing (P211620USI_ST25.txt; Size: 3.428 KB; and Date of Creation: Jan. 28, 2022) is herein incorporated by reference in its entirety.

BACKGROUND

Technical Field

The present invention relates to a white roselle (*Hibiscus sabdariffa* cv.) extract, and more particular to a method for enhancing skin moisture with a white roselle extract.

Related Art

Since the concept on organic and natural diets is increasingly prevalent, biotechnology companies and food industries have been intensively investing in the development of natural plant-related products. In order to provide a scientific evidence for the health benefits of plant-related product, the analysis of the active ingredients of plants and evaluation of their efficacy have become the focus of product development.

White roselle (*Hibiscus sabdariffa* cv.), also referred to as crystal roselle, white roselle flower, or white jade roselle, is a species in the genus *Hibiscus* in the family Malvaceae. White roselle is an annual herb or a perennial shrub, growing to about 1-2 m in tropical and subtropical regions. It can be used to reduce heat and relieve inflammation, refresh and relieve fatigue, regulate blood lipids, reduce blood pressure, and reduce cholesterol.

SUMMARY

In some embodiments, a method for enhancing skin moisture is provided, including administering to a subject in need thereof a composition including a white roselle (*Hibiscus sabdariffa* cv.) extract. The white roselle extract is obtained by lysing a cell wall of a white roselle calyx by ice crystals and extracting the lysed white roselle calyx with a solvent.

In conclusion, the white roselle extract of any embodiments can prepare a composition for enhancing skin moisture. In other words, the composition has the function of enhancing skin moisture.

DETAILED DESCRIPTION

Figure 1:
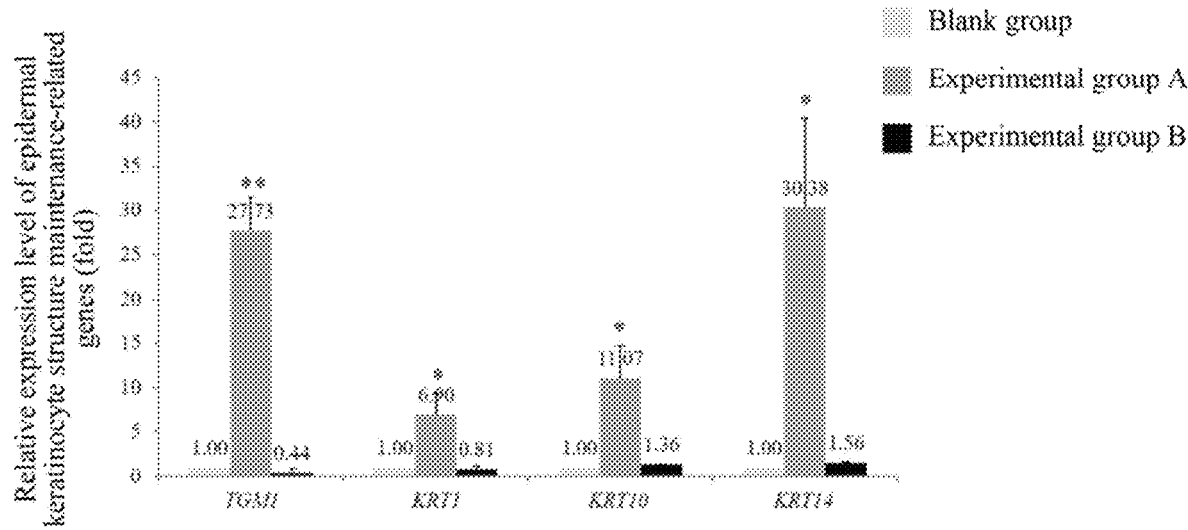
FIG. 1 is a graph showing folds of relative expression level of epidermal keratinocyte structure maintenance-related genes in Blank group, Experimental group A and B in some embodiments of the present invention.

The following will describe some specific implementations of the present invention. Without departing from the spirit of the present invention, the present invention can still be practiced in many different forms, and the protection scope should not be limited to the conditions specified in this specification.

In some embodiments, a white roselle extract obtained from the calyx of white roselle (*Hibiscus sabdariffa* cv.) has the capability of enhancing skin moisture. Therefore, a method for enhancing skin moisture in a subject in need thereof, comprising administering to the subject a composition comprising a white roselle extract. The white roselle extract is obtained by lysing a cell wall of a white roselle calyx by ice crystals prior to the extraction of the lysed white roselle calyx with a solvent.

In some embodiments, in the process of extraction, the white roselle calyx is frozen at −20±5° C., so that the cell wall of the white roselle calyx is lysed by ice crystals, and the extraction is carried out on the white roselle calyx with the lysed cell wall at 85±5° C. with water for 60-90 min, so as to obtain a primary extract. For example, the white roselle calyx is soaked in water with a volume 5 folds of the volume of the calyx at 85±5° C. for 60-90 min.

In some embodiments, the white roselle calyx for extraction may be whole or separated into fragments, granules, or powder by physical pre-processing. The physical pre-processing used may include at least one of the following: coarse crushing, chopping, shearing, mashing, and grinding.

In some embodiments, the white roselle calyx is frozen at −20±5° C. for more than 24 h, so that the water contained in the calyx forms ice crystals due to rapid freezing. The formed ice crystals can break the cell wall of the calyx to release more active substances.

In some embodiments, in the process of extraction, the primary extract may be further filtered to remove impurities, so as to obtain a filtrate. In some embodiments, during the process of extraction, the filtrate may be further concentrated to obtain a concentrate. In some embodiments, during the process of extraction, the concentrate may be further filtered to obtain a concentrated filtrate.

In some embodiments, the concentration is carried out at 60±5° C.

In other words, the primary extract, the filtrate, the concentrate, or the concentrated filtrate obtained in the process of extraction may be used as a white roselle extract according to actual needs.

In some embodiments, the white roselle extract contributes to the enhancement of skin moisture by increasing an expression level of epidermal keratinocyte structure maintenance-related genes.

In some embodiments, the epidermal keratinocyte structure maintenance-related genes include transglutaminase 1 (TGM1) gene and keratin (KRT) gene. The KRT gene may be at least one of the following: KRT1 gene, KRT10 gene, and KRT14 gene.

In some embodiments, the white roselle extract contributes to the enhancement of skin moisture by increasing aquaporins.

In some embodiments, the white roselle extract contributes to the enhancement of skin moisture by increasing an expression level of aquaporin genes.

In some embodiments, the aquaporin gene may be aquaporin 3 (AQP3) gene.

In some embodiments, the white roselle extract contributes to the enhancement of skin moisture by increasing ceramides.

In some embodiments, the white roselle extract contributes to the enhancement of skin moisture by increasing ceramide generation-related genes.

In some embodiments, the ceramide generation-related genes include glucosylceramidase (GBA) gene and sphingomyelin phosphodiesterase 1 (SMPD1) gene.

In some embodiments, the white roselle extract contributes to the enhancement of skin moisture by increasing hyaluronic acid secretion.

In some embodiments, the white roselle extract contributes to the enhancement of skin moisture by increasing an expression level of hyaluronic acid synthesis-related genes.

In some embodiments, the hyaluronic acid synthesis-related gene may be hyaluronan synthase (HAS) gene. The HAS gene includes HAS2 gene and HAS3 gene.

In some embodiments, an effective dose of the white roselle extract is 1.5 mg/day.

In some embodiments, a method for enhancing skin moisture is provided, including administering to a subject in need thereof a composition including a white roselle (*Hibiscus sabdariffa* cv.) extract, and the composition prepared may be a pharmaceutical composition, a food composition, a cosmetic composition, or a cosmeceutical composition.

In some embodiments, the composition is a pharmaceutical composition containing an effective content of the white roselle extract. In particular, the pharmaceutical composition may be manufactured into a dosage form suitable for enteral, parenteral, oral, or topical administration by using techniques well known to those skilled in the art.

In some embodiments, the dosage form for enteral or oral administration includes, but is not limited to: a tablet, a troche, a lozenge, a pill, a capsule, a dispersible powder or granule, a solution, a suspension, an emulsion, a syrup, an elixir, a slurry, or other similar substances. In some embodiments, the dosage form for parenteral or topical administration includes, but is not limited to: an injection, a sterile powder, an external preparation, or other similar substances. In some embodiments, the administration manner of the injection may be subcutaneous injection, intraepidermal injection, intradermal injection, or intralesional injection.

In some embodiments, the pharmaceutical composition containing the white roselle extract may further include a pharmaceutically acceptable carrier that is widely used in pharmaceutical manufacturing technology. In some embodiments, the pharmaceutically acceptable carrier may be one or more of the following carriers: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, or other similar substances. The type and quantity of selected carriers are within the expertise and routine of those skilled in the art. In particularly, the solvent of the pharmaceutically acceptable carrier can be water, normal saline, phosphate buffered saline (PBS), or alcohol containing aqueous solution.

In some embodiments, the composition is a food composition containing a specific content of white roselle extract. The food composition may be in the form of powder, granule, solution, colloid, or paste.

In some embodiments, the food composition containing the white roselle extract may be a food product or a food additive.

In some embodiments, the food product containing the white roselle extract may be beverages, fermented foods, bakery products, health foods, dietary supplements, or the like. In some embodiments, the food product containing the white roselle extract may further include an adjuvant. For example, the adjuvant may be maltodextrin, malic acid, sucralose, citric acid, fruit flavor, honey flavor steviol glycoside, or a combination thereof. The type and quantity of selected carriers are within the expertise and routine of those skilled in the art.

In some embodiments, the food additive containing the white roselle extract may be a condiment, a sweetener, a flavor, a pH adjuster, an emulsifier, a colorant, a stabilizer, or the like.

In some embodiments, the aforementioned composition may be a cosmetic composition or a cosmeceutical composition. In other words, the cosmetic or cosmeceutical composition contains a specific content of white roselle extract.

In some embodiments, the cosmetic or cosmeceutical composition containing the white roselle extract may be in any of the following forms: toner, gel, jelly mask, mud mask, lotion, cream, lipstick, foundation, pressed powder, face powder, cleansing oil, cleansing milk, facial cleanser, body wash, shampoo, hair conditioner, sunscreen, hand cream, nail polish, perfume, essence, and facial mask.

In some embodiments, the cosmetic or cosmeceutical composition containing the white roselle extract may further contain acceptable ingredients for external products as required. In some embodiments, the acceptable ingredients for external products may be, for example, an emulsifier, a penetration enhancer, an emollient, a solvent, an excipient, an antioxidant, or a combination thereof.

Unless otherwise specified, the experimental steps in the following examples are carried out at room temperature (25±5° C.) and atmospheric pressure (1 atm).

Example 1: Preparation of White Roselle Extract and Roselle Extract

Raw Materials:
1. White roselle (*Hibiscus sabdariffa* cv.) calyx, originating in Pingtung, Taiwan, purchased from Ye Junhong, a local farmer.
2. Roselle (*Hibiscus sabdariffa* Linn. Sp. Pl.) calyx, originating in Pingtung, Taiwan, purchased from Ye Junhong, a local farmer.
3. Secondary water, also referred to as RO water or secondary distilled water.

Preparation Process:
1. The white roselle calyx was placed in a freezer for 24 h to allow ice crystals to break the cell wall of the white roselle calyx. The temperature of the freezer was set to be −20±5° C.
2. The white roselle calyx with the lysed cell wall was coarsely crushed by a blender (model: 10 Speed Blender; brand: Osterizer), and sieved by a 40-mesh sieve, so as to obtain a coarse white roselle product.
3. The coarse white roselle product was added into the secondary water heated to 85±5° C., to carry out extraction on the coarse white roselle product for 60 min in a weight ratio of coarse white roselle product to secondary water of 1:5 at 85±5° C., to obtain a primary extract.
4. The primary extract was filtered with a 400-mesh filter to obtain a filtrate.
5. The filtrate was concentrated under reduced pressure by a concentrator (model: Rotavapor R-100; brand: BUCHI) with a temperature set to be 60° C. to obtain a concentrate.
6. The concentrate was filtered with a 400-mesh filter to obtain a concentrated filtrate. Herein, the concentrated filtrate was used as a white roselle extract for use in subsequent experiments. The sugar content of the concentrated filtrate was Brix 8.0±0.3.
7. A roselle extract was prepared from the roselle calyx according to the Step 1 to Step 6 in the foregoing preparation process.
8. The prepared white roselle extract and roselle extract were stored in a freezer for subsequent testing.

Example 2: Test of Expression Level of Epidermal Keratinocyte Structure Maintenance-Related Genes Materials and Instruments:
1. Cell strain: human primary epidermal keratinocytes, purchased from ATCC, cell number PCS-200-011, hereinafter referred to as HPEK-50 cells.
2. Culture medium: serum-free medium for keratinocytes (Keratinocyte-SFM), purchased from Thermo, product number 17005042.
3. RNA extraction reagent kit, purchased from TANBead, product number 6K206.
4. SuperScript® III reverse transcriptase, purchased from Invitrogene, product number 18080-044.
5. ABI StepOnePlus™ Real-Time PCR system, purchased from Thermo Fisher Scientific.
6. KAPA SYBR FAST qPCR Master Mix (2×) Kit, purchased from KAPA Biosystems, product number KK4600.

Test Process:
1. HPEK-50 cells were seeded in a 6-well culture plate containing 2 mL of culture medium per well in a density of 1×10$^5$ cells per well, and cultured at 37° C. for 24 h.
2. After the culture, the HPEK-50 cells were divided into the following three groups: a blank group, an experimental group A, and an experimental group B. The culture medium of the blank group contained no extract; the culture medium of the experimental group A contained 0.25% (v/v) white roselle extract prepared in Example 1; and the culture medium of the experimental group B contained 0.25% (v/v) roselle extract prepared in Example 1. Each group was triplicated and then cultured at 37° C. for 24 h.
3. After the culture, the culture media of the blank group, experimental group A, and experimental group B were removed, and the cells were rinsed with PBS.
4. After the rinse, the cell membranes of the HPEK-50 cells in each group were lysed with a cell lysis buffer from an RNA extraction reagent kit to form a cell solution.
5. In each group, RNA was extracted from the cell solution by using the RNA extraction reagent kit.
6. In each group, 2000 ng of the extracted RNA was used as a template, and reverse-transcribed with SuperScript® III reverse transcriptase into corresponding cDNA.
7. The quantitative real-time reverse transcription polymerase chain reaction was carried out on the cDNA with the primers in Table 1 by using the ABI StepOnePlus™ Real-Time PCR system and the KAPA SYBR FAST qPCR Master Mix (2×) Kit to observe the expression level of various target genes of the HPEK-50 cells in the blank group, experimental group A, and experimental group B, and to obtain a melting curve thereof. The instrument setting conditions for the quantitative real-time reverse transcription polymerase chain reaction were 95° C., for 20 s, 95° C. for 3 s, 60° C. for 30 s with 40 repetitive cycles.
8. The relative expression level of the target gene was determined by the $2^{-\Delta\Delta Ct}$ method. The relative expression level was defined as a fold change of the RNA expression level of a target gene in the experimental group relative to the same gene in the blank group. The $2^{-\Delta\Delta Ct}$ method used the cycle threshold (Ct) of the TBP gene as the Ct of the reference gene of the internal control, and calculated the fold change according to the following formula:

$$\Delta Ct = Ct_{target\ gene\ of\ experimental\ group}\ target\ gene\ of\ blank\ group - Ct_{TBP}$$

$$\Delta\Delta Ct = \Delta Ct_{target\ gene\ of\ experimental\ group} - \Delta Ct_{target\ gene\ of\ blank\ group}$$

$$\text{Fold change} = 2^{-\Delta\Delta Ct\ average}$$

TABLE 1

| Primer name | Sequence number | Sequence |
|---|---|---|
| TGM1-F | SEQ ID NO: 1 | GATCGCATCACCCTTGAGTTAC |
| TGM1-R | SEQ ID NO: 2 | GCAGGTTCAGATTCTGCCC |
| KRT1-F | SEQ ID NO: 3 | AGAGTGGACCAACTGAAGAGT |

TABLE 1-continued

| Primer name | Sequence number | Sequence |
|---|---|---|
| KRT1-R | SEQ ID NO: 4 | ATTCTCTGCATTTGTCCGCTT |
| KRT10-F | SEQ ID NO: 5 | TCCTACTTGGACAAAGTTCGGG |
| KRT10-R | SEQ ID NO: 6 | CCCCTGATGTGAGTTGCCA |
| KRT14-F | SEQ ID NO: 7 | TTCTGAACGAGATGCGTGAC |
| KRT14-R | SEQ ID NO: 8 | GCAGCTCAATCTCCAGGTTC |

9. The statistically significant difference of the determination results between the blank group and the experimental group was analyzed by student's t-test. (In the figures, "*" represents a p value less than 0.05 in comparison with the blank group, "" represents a p value less than 0.01 in comparison with the blank group, and "*" represents a p value less than 0.001 in comparison with the blank group. More "*" represents more significant statistical differences.)

Test Results:

Refer to FIG. 1. An expression level of genes of the HPEK-50 cells untreated with the white roselle extract or the roselle extract in the blank group, that was, under normal physiological metabolism, was regarded as 1. Compared with the blank group, the relative expression level of TGM1 gene in the experimental group A (with the white roselle extract) was 27.73, and the relative expression level of TGM1 gene in the experimental group B (with the roselle extract) was 0.44; the relative expression level of KRT1 gene in the experimental group A (with the white roselle extract) was 6.90, and the relative expression level of KRT1 gene in the experimental group B (with the roselle extract) was 0.81; the relative expression level of KRT10 gene in the experimental group A (with the white roselle extract) was 11.07, and the relative expression level of KRT10 gene in the experimental group B (with the roselle extract) was 1.36; and the relative expression level of KRT14 gene in the experimental group A (with the white roselle extract) was 30.38, and the relative expression level of KRT14 gene in the experimental group B (with the roselle extract) was 1.56.

It can be learned that the white roselle extract, different from the roselle extract, can significantly increase the expression level of the TGM1 gene and KRT1 gene, while the roselle extract reduces the expression level of the TGM1 gene and KRT1 gene. In addition, the white roselle extract can significantly increase the expression level of the KRT10 gene and KRT14 gene, better than the roselle extract.

Example 3: Test of Expression Level of Aquaporin Genes

Materials and Instruments:
1. Cell strain: human primary epidermal keratinocytes, purchased from ATCC, cell number PCS-200-011, hereinafter referred to as HPEK-50 cells.
2. Culture medium: serum-free medium for keratinocytes (Keratinocyte-SFM), purchased from Thermo, product number 17005042.
3. RNA extraction reagent kit, purchased from TANBead, product number 6K206.
4. SuperScript® III reverse transcriptase, purchased from Invitrogene, product number 18080-044.
5. ABI StepOnePlus™ Real-Time PCR system, purchased from Thermo Fisher Scientific.
6. KAPA SYBR FAST qPCR Master Mix (2×) Kit, purchased from KAPA Biosystems, product number KK4600.

Test Process:
1. HPEK-50 cells were seeded in a 6-well culture plate containing 2 mL of culture medium per well in a density of $1\times10^5$ cells per well, and cultured at 37° C. for 24 h.
2. After the culture, the HPEK-50 cells were divided into the following three groups: a blank group, an experimental group A, and an experimental group B. The culture medium of the blank group contained no extract; the culture medium of the experimental group A contained 0.25% (v/v) white roselle extract prepared in Example 1; and the culture medium of the experimental group B contained 0.25% (v/v) roselle extract prepared in Example 1. Each group was triplicated and then cultured at 37° C. for 24 h.
3. After the culture, the culture media of the blank group, experimental group A, and experimental group B were removed, and the cells were rinsed with PBS.
4. After the rinse, the cell membranes of the HPEK-50 cells in each group were lysed with a cell lysis buffer from an RNA extraction reagent kit to form a cell solution.
5. In each group, RNA was extracted from the cell solution by using the RNA extraction reagent kit.
6. In each group, 2000 ng of the extracted RNA was used as a template, and reverse-transcribed with SuperScript® III reverse transcriptase into corresponding cDNA.
7. The quantitative real-time reverse transcription polymerase chain reaction was carried out on the cDNA with the primers in Table 2 by using the ABI StepOnePlus™ Real-Time PCR system and the KAPA SYBR FAST qPCR Master Mix (2×) Kit to observe the expression level of various target genes of the HPEK-50 cells in the blank group, experimental group A, and experimental group B, and to obtain a melting curve thereof. The instrument setting conditions for the quantitative real-time reverse transcription polymerase chain reaction were 95° C. for 20 s, 95° (for 3 s, 60° (for 30 s with 40 repetitive cycles.
8. The relative expression level of the target gene was determined by the $2^{-\Delta\Delta Ct}$ method. The relative expression level is defined as a fold change of the RNA expression level of a target gene in the experimental group relative to the same gene in the blank group. The $2^{-\Delta\Delta Ct}$ method used the cycle threshold (Ct) of the TBP gene as the Ct of the reference gene of the internal control, and calculated the fold change according to the following formula:

$$\Delta Ct = Ct_{target\ gene\ of\ experimental\ group} - Ct_{target\ gene\ of\ blank\ group} - Ct_{TBP}$$

$$\Delta\Delta Ct = \Delta Ct_{target\ gene\ of\ experimental\ group} - \Delta Ct_{target\ gene\ of\ blank\ group}$$

$$\text{Fold change} = 2^{-\Delta\Delta Ct\ average}$$

TABLE 2

| Primer name | Sequence number | Sequence |
|---|---|---|
| AQP3-F | SEQ ID NO: 9 | GGGGAGATGCTCCACATCC |
| AQP3-R | SEQ ID NO: 10 | AAAGGCCAGGTTGATGGTGAG |

9. The statistically significant difference of the determination results between the blank group and the experimental group was analyzed by student's t-test. (In the figures, "*" represents a p value less than 0.05 in comparison with the blank group, "" represents a p value less than 0.01 in comparison with the blank group, and "*" represents a p value less than 0.001 in comparison with the blank group. More "*" represents more significant statistical differences.)

Figure 2:
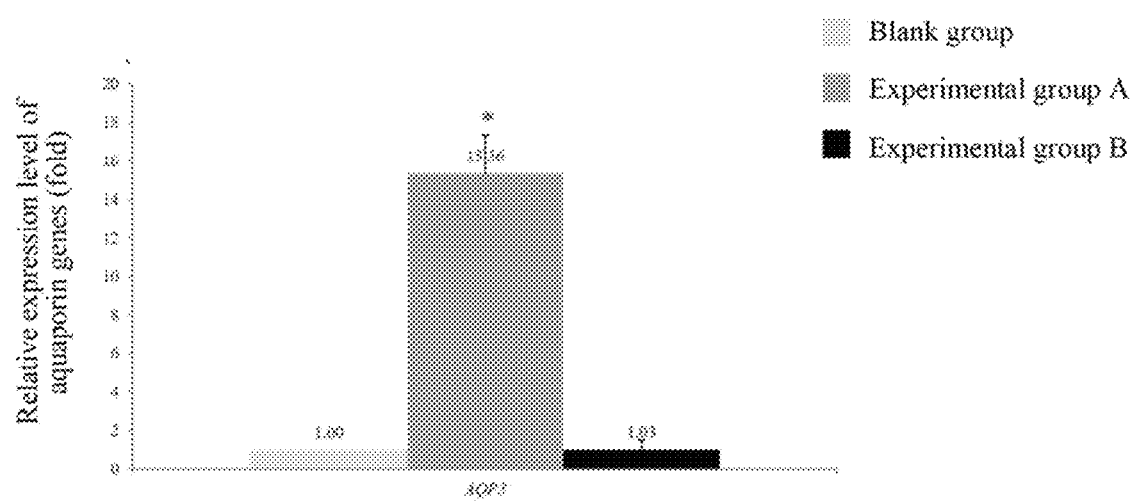
FIG. 2 is a graph showing folds of relative expression level of aquaporin genes in Blank group, Experimental group A and B in some embodiments of the present invention.

Test Results:

Refer to FIG. 2. An expression level of genes of the HPEK-50 cells untreated with the white roselle extract or the roselle extract in the blank group, that was, under normal physiological metabolism, was regarded as 1. Compared with the blank group, the relative expression level of AQP3 gene in the experimental group A (with the white roselle extract) was 15.36, and the relative expression level of AQP3 gene in the experimental group B (with the roselle extract) was 1.03.

It can be learned that the white roselle extract can significantly increase the expression level of the AQP3 gene, better than the roselle extract.

Example 4: Test of Expression Level of Ceramide Generation-Related Genes

Materials and Instruments:
1. Cell strain: human primary epidermal keratinocytes, purchased from ATCC, cell number PCS-200-011, hereinafter referred to as HPEK-50 cells.
2. Culture medium: serum-free medium for keratinocytes (Keratinocyte-SFM), purchased from Thermo, product number 17005042.
3. RNA extraction reagent kit, purchased from TANBead, product number 6K206.
4. SuperScript® III reverse transcriptase, purchased from Invitrogene, product number 18080-044.
5. ABI StepOnePlus™ Real-Time PCR system, purchased from Thermo Fisher Scientific.
6. KAPA SYBR FAST qPCR Master Mix (2×) Kit, purchased from KAPA Biosystems, product number KK4600.

Test Process:
1. HPEK-50 cells were seeded in a 6-well culture plate containing 2 mL of culture medium per well in a density of 1×10³ cells per well, and cultured at 37° C. for 24 h.
2. After the culture, the HPEK-50 cells were divided into the following three groups: a blank group, an experimental group A, and an experimental group B. The culture medium of the blank group contained no extract; the culture medium of the experimental group A contained 0.25% (v/v) white roselle extract prepared in Example 1; and the culture medium of the experimental group B contained 0.25% (v/v) roselle extract prepared in Example 1. Each group was triplicated and then cultured at 37° C. for 24 h.
3. After the culture, the culture media of the blank group, experimental group A, and experimental group B were removed, and the cells were rinsed with PBS.
4. After the rinse, the cell membranes of the HPEK-50 cells in each group were lysed with a cell lysis buffer from an RNA extraction reagent kit to form a cell solution.
5. In each group, RNA was extracted from the cell solution by using the RNA extraction reagent kit.
6. In each group, 2000 ng of the extracted RNA was used as a template, and reverse-transcribed with SuperScript® III reverse transcriptase into corresponding cDNA.
7. The quantitative real-time reverse transcription polymerase chain reaction was carried out on the cDNA with the primers in Table 3 by using the ABI StepOnePlus™ Real-Time PCR system and the KAPA SYBR FAST qPCR Master Mix (2×) Kit to observe the expression level of various target genes of the HPEK-50 cells in the blank group, experimental group A, and experimental group B, and to obtain a melting curve thereof. The instrument setting conditions for the quantitative real-time reverse transcription polymerase chain reaction were 95° C. for 20 s, 95° C. for 3 s, 60° C. for 30 s with 40 repetitive cycles.
8. The relative expression level of the target gene was determined by the $2^{-\Delta\Delta Ct}$ method. The relative expression level is defined as a fold change of the RNA expression level of a target gene in the experimental group relative to the same gene in the blank group. The $2^{-\Delta\Delta Ct}$ method used the cycle threshold (Ct) of the TBP gene as the Ct of the reference gene of the internal control, and calculated the fold change according to the following formula:

$$\Delta Ct = Ct_{target\ gene\ of\ experimental\ group\ target\ gene\ of\ blank\ group} - Ct_{TBP}$$

$$\Delta\Delta Ct = \Delta Ct_{target\ gene\ of\ experimental\ group} - \Delta Ct_{target\ gene\ of\ blank\ group}$$

Fold change = $2^{-\Delta\Delta Ct\ average}$

TABLE 3

| Primer name | Sequence number | Sequence |
|---|---|---|
| SMPD1-F | SEQ ID NO: 11 | CTGACTCTCGGGTTCTCTGG |
| SMPD1-R | SEQ ID NO: 12 | TCCACCATGTCATCCTCAAA |
| GBA-F | SEQ ID NO: 13 | TCCAGTTGCACAACTTCAGC |
| GBA-R | SEQ ID NO: 14 | TTGTGCTCAGCATAGGCATC |

9. The statistically significant difference of the determination results between the blank group and the experimental group was analyzed by student's t-test. (in the figures, "*" represents a p value less than 0.05 in comparison with the blank group, "" represents a p value less than 0.01 in comparison with the blank group, and "*" represents a p value less than 0.001 in comparison with the blank group. More "*" represents more significant statistical differences.)

Figure 3:
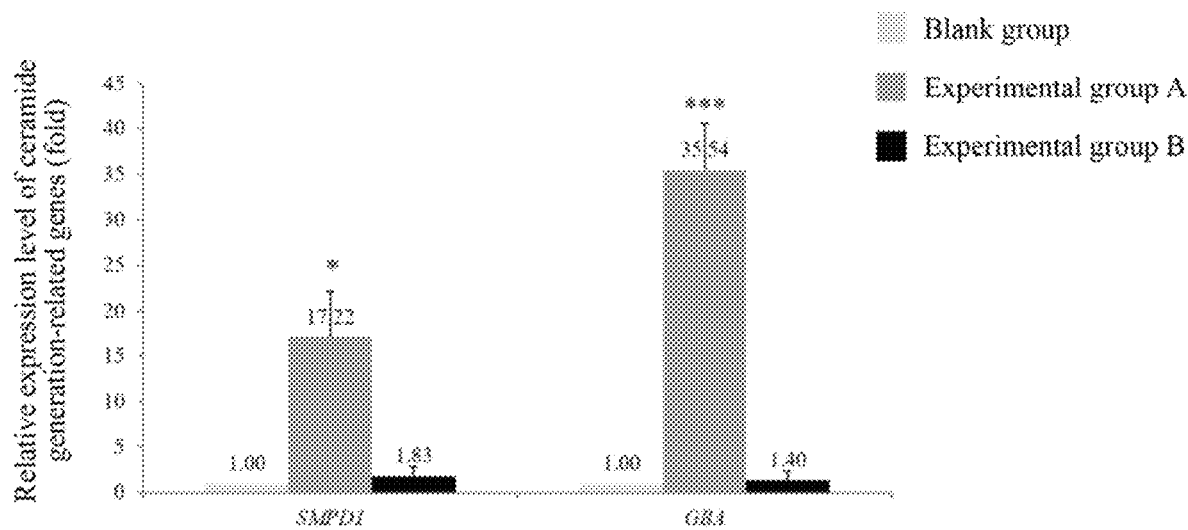
FIG. 3 is a graph showing folds of relative expression level of ceramide generation-related genes in Blank group, Experimental group A and B in some embodiments of the present invention.

Test Results:

Refer to FIG. 3. An expression level of genes of the HPEK-50 cells untreated with the white roselle extract or the roselle extract in the blank group, that was, under normal physiological metabolism, was regarded as 1. Compared with the blank group, the relative expression level of SMPD1 gene in the experimental group A (with the white roselle extract) was 17.22, and the relative expression level of SMPD1 gene in the experimental group B (with the roselle extract) was 1.83; and the relative expression level of GBA gene in the experimental group A (with the white roselle extract) was 35.54, and the relative expression level of GBA gene in the experimental group B (with the roselle extract) was 1.40.

It can be learned that the white roselle extract can significantly increase the expression level of the SMPD1 gene and GBA gene, better than the roselle extract.

Example 5: Test of expression level of hyaluronic acid synthesis-related genes

Materials and Instruments:
1. Cell strain: human primary epidermal keratinocytes, purchased from ATCC, cell number PCS-200-011, hereinafter referred to as HPEK-50 cells.
2. Culture medium: serum-free medium for keratinocytes (Keratinocyte-SFM), purchased from Thermo, product number 17005042.
3. RNA extraction reagent kit, purchased from TANBead, product number 6K206.
4. SuperScript® III reverse transcriptase, purchased from Invitrogene, product number 18080-044.
5. ABI StepOnePlus™ Real-Time PCR system, purchased from Thermo Fisher Scientific.
6. KAPA SYBR FAST qPCR Master Mix (2×) Kit, purchased from KAPA Biosystems, product number KK4600.

Test Process.
1. HPEK-50 cells were seeded in a 6-well culture plate containing 2 mL of culture medium per well in a density of $1 \times 10^5$ cells per well, and cultured at 37° C. for 24 h.
2. After the culture, the HPEK-50 cells were divided into the following three groups: a blank group, an experimental group A, and an experimental group B. The culture medium of the blank group contained no extract; the culture medium of the experimental group A contained 0.25% (v/v) white roselle extract prepared in Example 1; and the culture medium of the experimental group B contained 0.25% (v/v) roselle extract prepared in Example 1. Each group was triplicated and then cultured at 37° C. for 24 h.
3. After the culture, the culture media of the blank group, experimental group A. and experimental group B were removed, and the cells were rinsed with PBS.
4. After the rinse, the cell membranes of the HPEK-50 cells in each group were lysed with a cell lysis buffer from an RNA extraction reagent kit to form a cell solution.
5. In each group, RNA was extracted from the cell solution by using the RNA extraction reagent kit.
6. In each group, 2000 ng of the extracted RNA was used as a template, and reverse-transcribed with SuperScript® III reverse transcriptase into corresponding cDNA.
7. The quantitative real-time reverse transcription polymerase chain reaction was carried out on the cDNA with the primers in Table 4 by using the ABI StepOnePlus™ Real-Time PCR system and the KAPA SYBR FAST qPCR Master Mix (2×) Kit to observe the expression level of various target genes of the HPEK-50 cells in the blank group, experimental group A, and experimental group B, and to obtain a melting curve thereof. The instrument setting conditions for the quantitative real-time reverse transcription polymerase chain reaction were 95° C. for 20 s, 95° (for 3 s, 60° (for 30 s with 40 repetitive cycles.
8. The relative expression level of the target gene was determined by the $2^{-\Delta\Delta Ct}$ method. The relative expression level is defined as a fold change of the RNA expression level of a target gene in the experimental group relative to the same gene in the blank group. The $2^{-\Delta\Delta Ct}$ method used the cycle threshold (Ct) of the TBP gene as the Ct of the reference gene of the internal control, and calculated the fold change according to the following formula:

$\Delta Ct = Ct_{target\ gene\ of\ experimental\ group} - Ct_{target\ gene\ of\ blank\ group} - Ct_{TBP}$ $\Delta\Delta Ct = \Delta Ct_{target\ gene\ of\ experimental\ group} - \Delta Ct_{target\ gene\ of\ blank\ group}$ Fold change = $2^{-\Delta\Delta Ct\ average}$

TABLE 4

| Primer name | Sequence number | Sequence |
| --- | --- | --- |
| HAS2-F | SEQ ID NO: 15 | AAGAACAACTTCCACGAAAAGGG |
| HAS2-R | SEQ ID NO: 16 | GGCTGGGTCAAGCATAGTGT |
| HAS3-F | SEQ ID NO: 17 | CGCAGCAACTTCCATGAGG |
| HAS3-R | SEQ ID NO: 18 | AGTCGCACACCTGGATGTAGT |

9. The statistically significant difference of the determination results between the blank group and the experimental group was analyzed by student's t-test. (In the figures, "*" represents a p value less than 0.05 in comparison with the blank group, "" represents a p value less than 0.01 in comparison with the blank group, and "*" represents a p value less than 0.001 in comparison with the blank group. More "*" represents more significant statistical differences.)

Figure 4:
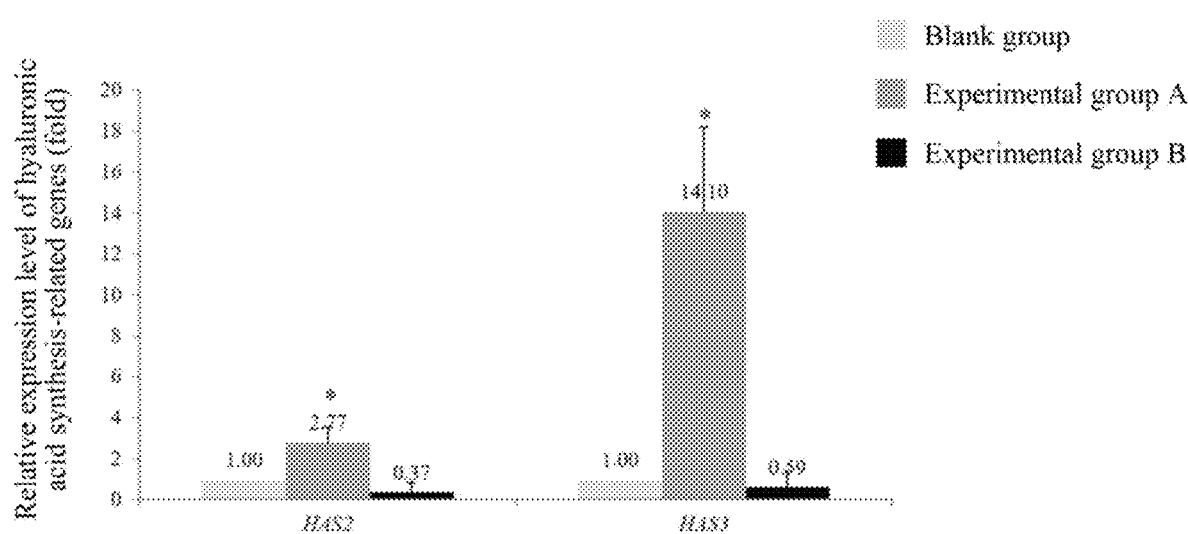
FIG. 4 is a graph showing folds of relative expression level of hyaluronic acid synthesis-related genes in Blank group, Experimental group A and B in some embodiments of the present invention.

Test Results:
Refer to FIG. 4. An expression level of genes of the HPEK-50 cells untreated with the white roselle extract or the roselle extract in the blank group, that was, under normal physiological metabolism, was regarded as 1. Compared with the blank group, the relative expression level of HAS2 gene in the experimental group A (with the white roselle extract) was 2.77, and the relative expression level of HAS2 gene in the experimental group B (with the roselle extract) was 0.37; and the relative expression level of HAS3 gene in the experimental group A (with the white roselle extract) was 14.10, and the relative expression level of HAS3 gene in the experimental group B (with the roselle extract) was 0.59.

It can be learned that the white roselle extract, different from the roselle extract, can significantly increase the expression level of the HAS2 gene and HAS3 gene, while the roselle extract reduces the expression level of the HAS2 gene and HAS3 gene.

Example 6: Test of Hyaluronic Acid Secretion

Materials and Instruments:
1. Cell strain: human primary epidermal keratinocytes, purchased from ATCC, hereinafter referred to as HPEK-50 cells.
2. Culture medium: serum-free medium for keratinocytes (Keratinocyte-SFM), purchased from Thermo, product number 17005042.
3. Human hyaluronic acid (HA) ELISA kit, purchased from Cusabio Biotech.
4. ELISA reader, purchased from BioTek (US).
5. White roselle extract and roselle extract, prepared by the method in Example 1 of the disclosure.

Test Process:
1. HPEK-50 cells were seeded in a 96-well culture plate containing 100 μL of culture medium per well in a density of 1×10⁴ cells per well, and divided into the following three groups: a blank group, an experimental group A, and an experimental group B. The culture medium of the blank group contained no extract; the culture medium of the experimental group A contained 0.0625% (v/v) white roselle extract prepared in Example 1; and the culture medium of the experimental group B contained 0.0625% (v/v) roselle extract prepared in Example 1. Each group was triplicated and then cultured at 37° C. for 24 h.
3. 100 μL. of culture medium from each well was added into a pre-coated ELISA plate, and cultured at 37° C. for 2 h.
4. The culture medium was removed from each well, and each well was not washed.
5. 100 μL of biotin-antibody was added into each well, and cultured at 37° C. for 1 h.
6. After the reaction was completed, the culture medium was removed from each well. Each well was washed with 200 μL of wash buffer and then allowed to stand for 2 min. This washing step was repeated for three times. After the last wash was completed, all remaining wash buffer was removed by suction.
7. 100 μL of HRP-avidin was added into each well, and cultured at 37° C. for 1 h.
8. After the reaction was completed, the culture medium was removed from each well. Each well was washed with 200 μL of wash buffer and then allowed to stand for 2 min. This washing step was repeated for five times. After the last wash was completed, all remaining wash buffer was removed by suction.
9. 90 μL of TMB substrate was added into each well to react in the dark at 37° C. for 30 min.
10. 50 μL of stop solution was added into each well, and the culture plate was gently tapped to ensure adequate mixing.
11. An absorbance at 450 nm was measured in each well within 5 min by using an ELISA reader.
12. The statistically significant difference of the determination results between the blank group and the experimental group was analyzed by student's t-test. (In the figures, "*" represents a p value less than 0.05 in comparison with the blank group, "" represents a p value less than 0.01 in comparison with the blank group, and "*" represents a p value less than 0.001 in comparison with the blank group. More "*" represents more significant statistical differences.)

Figure 5:
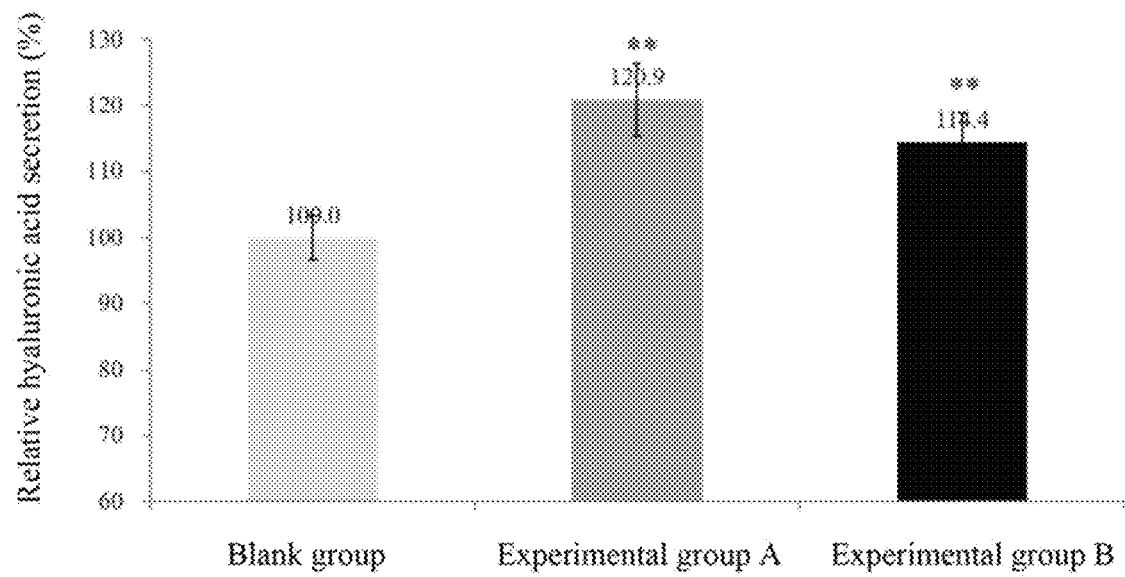
FIG. 5 is a graph showing percentages of relative secretion of hyaluronic acid in Blank group, Experimental group A and B in some embodiments of the present invention.

Test Results:
Refer to FIG. 5. An amount of hyaluronic acid produced by the HPEK-50 cells untreated with the white roselle extract or the roselle extract in the blank group, that was, under normal physiological metabolism, was regarded as 100%. Relative to the blank group, an amount of hyaluronic acid produced by the HPEK-50 cells treated with the white roselle extract in the experimental group A was 120.9%. Relative to the blank group, an amount of hyaluronic acid produced by the HPEK-50 cells treated with the roselle extract in the experimental group B was 114.4%. In other words, compared with the blank group, the relative hyaluronic acid secretion rates of both the experimental group A and the experimental group B increased. Compared with the blank group, the relative hyaluronic acid secretion of the experimental group A (with the white roselle extract) was increased by 20.9%. Compared with the blank group, the relative hyaluronic acid secretion of the experimental group B (with the roselle extract) was increased by 14.4%. It can be learned that both the white roselle extract and the roselle extract can significantly promote the production of hyaluronic acid in HPEK-50 cells, and the capability of white roselle extract to increase hyaluronic acid secretion is better than that of the roselle extract. Based on this, the white roselle extract has the effect of promoting hyaluronic acid secretion, which is beneficial to retain skin collagen, increase skin moisture content, and provide skin elasticity and flexibility.

Hyaluronic acid can prevent natural aging of the skin, and protect the skin from the damage caused by the sun's ultraviolet rays, tobacco smoke, and air pollutants. Hyaluronic acid can also help increase skin moisture, so that the skin structure is firm and plump, so as to reduce skin fine texture and wrinkles. In addition, hyaluronic acid also plays a key role in wound healing. When skin cells need to be repaired or are damaged, the concentration of hyaluronic acid will also increase, and its use on skin wounds has been proven to reduce the size of the wound and relieve pain. It can also help reduce the risk of wound cell infection.

Moreover, hyaluronic acid is also helpful for osteoarthritis. It is shown from literatures that consuming 80-200 mg of hyaluronic acid every day for at least two months can significantly relieve the knee joint pain in patients with osteoarthritis. Hyaluronic acid can also help relieve gastric acid reflux symptoms. Hyaluronic acid has excellent moisturizing properties, so that it is also commonly used to treat dry eye syndrome, slow down osteoporosis, relieve bladder pain syndrome, and the like.

Example 7: Human Subject Experiment-Test of Improving Skin Condition

Nine healthy adult subjects aged 25-55 were asked to drink a 50 g white roselle extract drink (containing 1.5 g of the white roselle extract prepared in Example 1) every day for four weeks (equal to 28 days).

Before drinking (the face was clean, week 0), after drinking for 14 days (the face was clean, week 2), and after drinking for 28 days (the face was clean, week 4), skin detection and skin condition questionnaire were carried out. The skin detection is to record values of the facial skin by corresponding devices and measurement methods, and to take photos before and after drinking. (When the detection was carried out before and after drinking, the temperature and humidity of the detection region where the subjects were located were consistent to reduce the influence of external temperature and humidity on the skin).

The skin was detected for the following detection items:
1. Skin Moisturizing Effect The facial skin of the same subject was detected before drinking the white roselle extract drink, after drinking for 14 days, and after drinking for 28 days by using a skin moisture content detection probe Corneometer® CM825 (C+K Multi Probe Adapter System, Germany) purchased from Courage+ Khazaka electronic, Germany. The detection probe is based on the principle of capacitance measurement. When the moisture content changes, the capacitance value of the skin also changes, so that the moisture content of the skin surface can be analyzed by measuring the capacitance value of the skin.

2. Transepidermal Water Loss (TEWL)

The facial skin of the same subject was detected before drinking the white roselle extract drink, after drinking for 14 days, and after drinking for 28 days by using a TEWL detection probe Tewameter® 0.300 (C+K Multi Probe Adapter System, Germany) purchased from Courage+ Khazaka electronic, Germany. The detection probe uses a cylindrical cavity with open ends to form a relatively stable test environment on the skin surface, and measures the water vapor pressure gradient at two different points to calculate the amount of water evaporated through the epidermis, so as to measure the water loss on the skin surface.

3. Skin Elasticity

The facial skin of the same subject was detected before drinking the white roselle extract drink, after drinking for 14 days, and after drinking for 28 days by using a skin physiological detector Soft Plus purchased from Callegari 1930, Italy. The test principle of the detector is that, based on the principle of suction and stretching, a negative pressure is generated on the surface of the skin to suck the skin into a test probe, the depth of the skin sucked into the probe is detected through the optical test system, and the skin elasticity is calculated by software analysis.

4. Skin Wrinkles

The facial skin of the same subject was detected before drinking the white roselle extract drink, after drinking for 14 days, and after drinking for 28 days by using a VISIA high class digital skin quality detector (VISIA Complexion Analysis System) purchased from Canfield scientific, US. The test principle of the detector is that the facial skin is photographed through a high-resolution camera lens, and the change of the skin shadow is detected by standard white light irradiation to detect the texture position and obtain a value that can represent the smoothness of the skin.

5. Collagen Density

The facial skin of the same subject was detected before drinking the white roselle extract drink, after drinking for 14 days, and after drinking for 28 days by using a high-frequency ultrasound detection probe (High Freq. Ultrasound Module) (DermaLab® USB Skin Analyzer, Denmark) purchased from Cortex Technology, Denmark. The detection probe transmitted acoustic pulses into the skin and converted the reflected signals of different intensities into different color markers. The lighter or brighter color indicates more collagen in the skin.

6. Skin Condition Questionnaire:

The skin condition questionnaire was carried out on the same subject before drinking the white roselle extract drink, after drinking for 14 days, and after drinking for 28 days. The skin condition questionnaire is self-assessment for dry and itchy skin, skin sagging, and lack of skin elasticity.

Test Results:

It is to be noted that the statistically significant difference of the determination between week 0 and week 2 and between week 0 and week 4 was analyzed by student's t-test. In the figures, "*" represents a p value less than 0.05 in comparison with week 0, "" represents a p value less than 0.01 in comparison with week 0, and "*" represents a p value less than 0.001 in comparison with week 0. More "*" represents more significant statistical differences.

Figure 6:
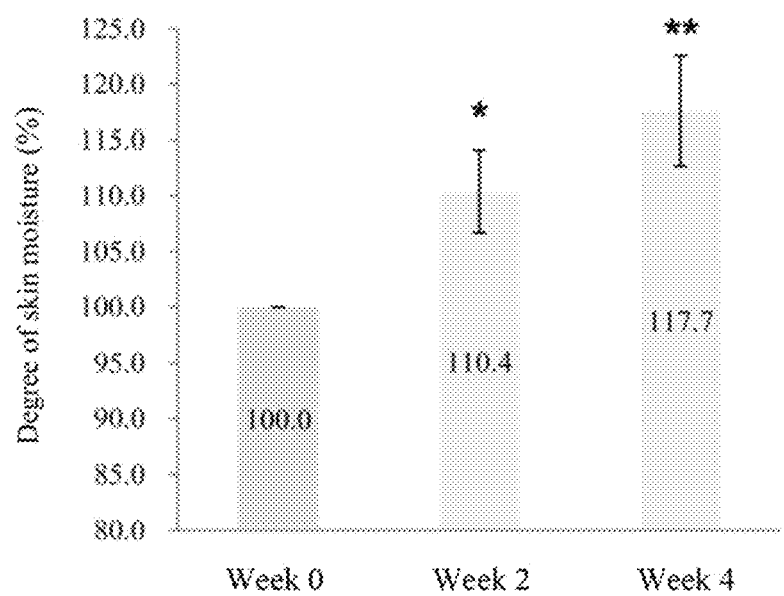
FIG. 6 is a graph showing percentages of detecting the degree of skin moisture at week 0, week 2, and week 4 in some embodiments of the present invention.

1. The test results of the "skin moisturizing effect" of the subjects are shown in FIG. 6. An average degree of skin moisture of nine subjects before drinking the white roselle extract drink (at week 0) obtained through detection by the skin moisture content detection probe Corneometer® CM825 was regarded as 100%. Average degrees of skin moisture of the subjects after drinking for 2 weeks and 4 weeks were 110.4% and 117.7% respectively. In other words, compared with no drinking of the white roselle extract drink (week 0), the degree of skin moisture of the subjects after drinking the drink containing 1.5 mL of white roselle extract for 2 weeks can be increased by 10.4%, and the degree of skin moisture of the subjects after drinking the drink containing 1.5 mL of white roselle extract for 4 weeks can be increased by 17.7%. It can be learned that the white roselle extract does have the capability of improving the degree of skin moisture.

Figure 7:
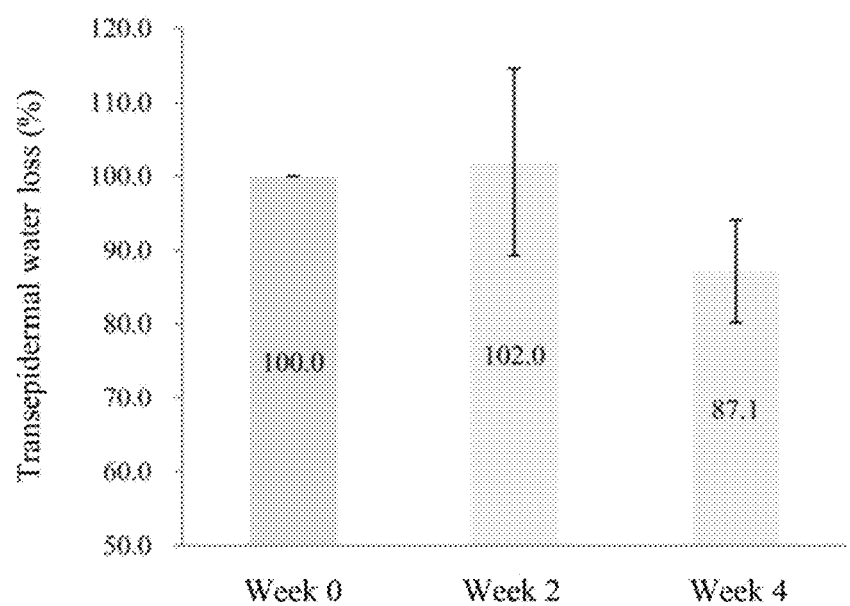
FIG. 7 is a graph showing percentages of detecting transepidermal water loss at week 0, week 2, and week 4 in some embodiments of the present invention.

2. The detection results of the "transepidermal water loss" of the subjects are shown in FIG. 7. An average TEWL of nine subjects before drinking the white roselle extract drink (at week 0) obtained through detection by the TEWL detection probe Tewameter® TM 300 was regarded as 100%. Average TEWL of the subjects after drinking for 2 weeks and 4 weeks were 102.0% and 87.1% respectively. In other words, compared with no drinking of the white roselle extract drink (week 0), the TEWL of the subjects after drinking the drink containing 1.5 mL of white roselle extract for 4 weeks can be reduced by 12.9%. It can be learned that the white roselle extract can indeed reduce the TEWL, thereby improving skin moisture, and has the potential to alleviate skin diseases related to abnormal TEWL values.

Figure 8:
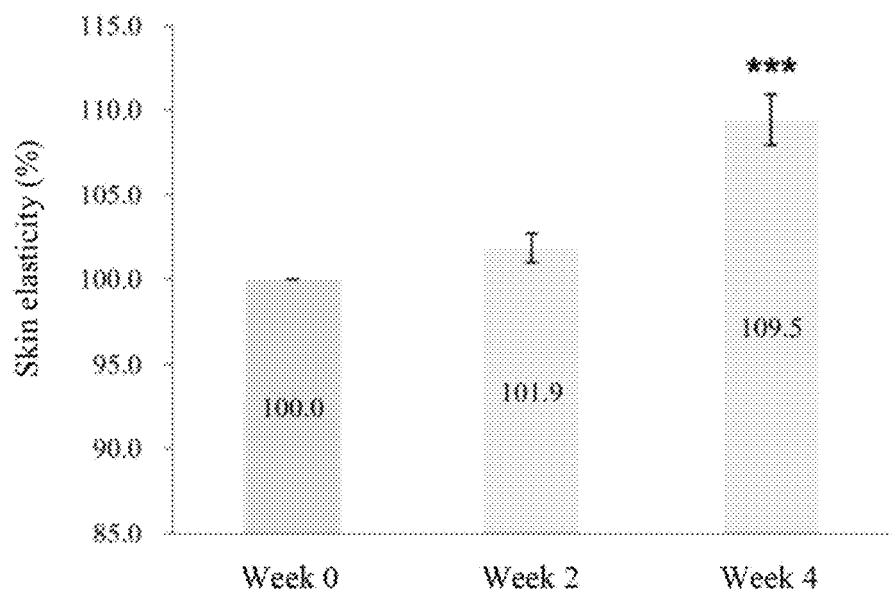
FIG. 8 is a graph showing percentages of detecting skin elasticity at week 0, week 2, and week 4 in some embodiments of the present invention.

3. The detection results of "skin elasticity" of the subjects are shown in FIG. 8. An average skin elasticity of nine subjects before drinking the white roselle extract drink (at week 0) obtained through detection by the skin physiological detector Soft Plus was regarded as 100%. Average skin elasticity of the subjects after drinking for 2 weeks and 4 weeks were 101.9% and 109.5% respectively. In other words, compared with no drinking of the white roselle extract drink (week 0), the skin elasticity of the subjects after drinking the drink containing 1.5 mL of white roselle extract for 2 weeks can be increased by 1.9%, and the skin elasticity of the subjects after drinking the drink containing 1.5 mL of white roselle extract for 4 weeks can be increased by 9.5%. It can be learned that the white roselle extract can indeed promote and improve the skin elasticity.

Figure 9:
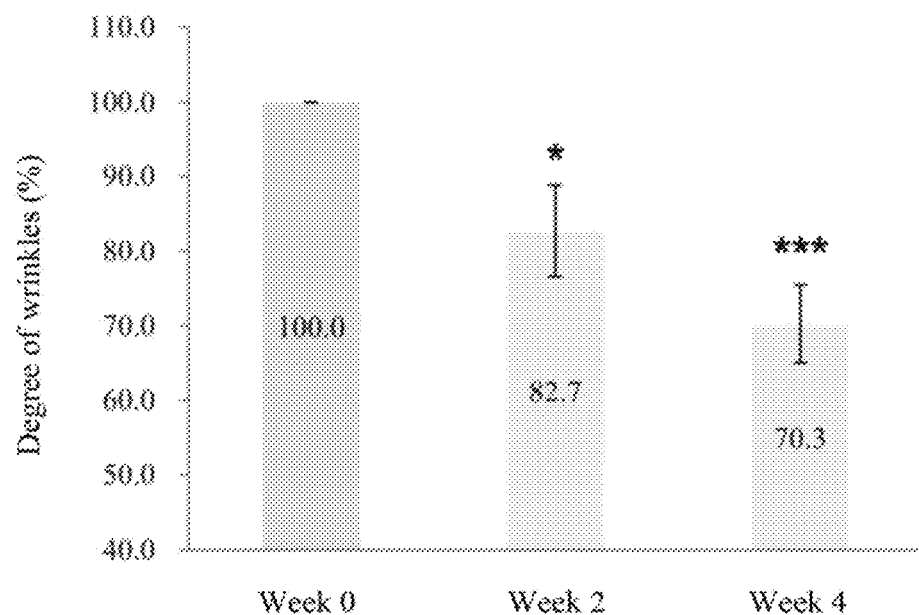
FIG. 9 is a graph showing percentages of detecting the degree of wrinkles at week 0, week 2, and week 4 in some embodiments of the present invention.

4. The detection results of "skin wrinkles" of the subjects are shown in FIG. 9. An average degree of wrinkles of nine subjects before drinking the white roselle extract drink (at week 0) obtained through detection by the VISIA high-end digital skin quality detector was regarded as 100%. Average degrees of wrinkles of the subjects after drinking for 2 weeks and 4 weeks were 82.7% and 70.3% respectively. In other words, compared with no drinking of the white roselle extract drink (week 0), the degree of wrinkles of the subjects after drinking the drink containing 1.5 mL of white roselle extract for 2 weeks can be reduced by 17.3%, and the degree of wrinkles of the subjects after drinking the drink containing 1.5 mL of white roselle extract for 4 weeks can be reduced by 29.7%. It can be learned that the white roselle extract can indeed reduce skin wrinkles and improve the skin condition of subjects, that is, the white roselle extract has the effect of smoothing fine wrinkles.

Figure 10:
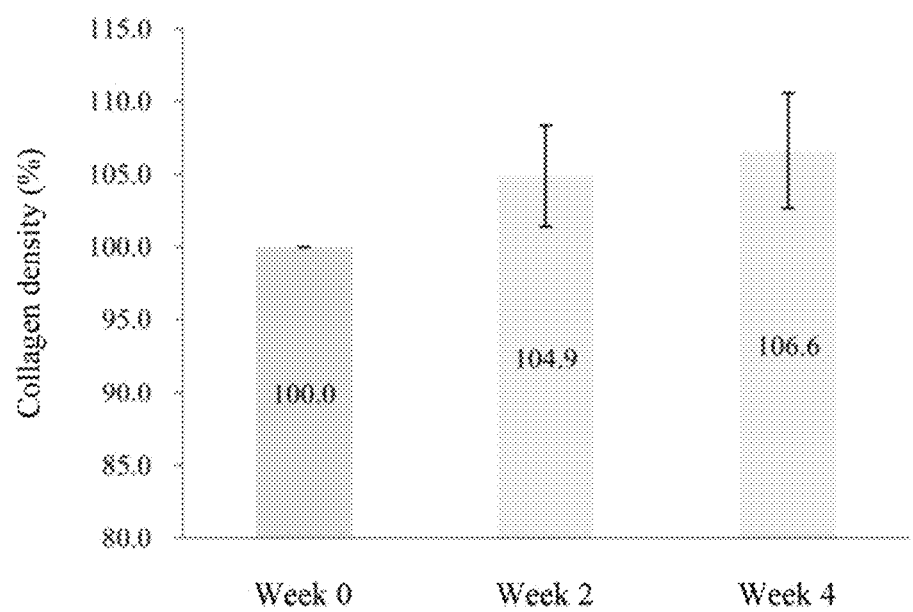
FIG. 10 is a graph showing percentages of detecting collagen density at week 0, week 2, and week 4 in some embodiments of the present invention.

5. The detection results of "collagen density" of the subjects are shown in FIG. 10. An average collagen density of nine subjects before drinking the white roselle extract drink (at week 0) obtained through detection by the high-frequency ultrasonic detection probe was regarded as 100%. Average collagen densities of the subjects after drinking for 2 weeks and 4 weeks were 104.9% and 106.6% respectively. In other words, compared with no drinking of the white roselle extract drink (week 0), the collagen density of the subjects after drinking the drink containing 1.5 mL of white roselle extract for 2 weeks can be increased by 4.9%, and the collagen density of the subjects after drinking the drink containing 1.5 mL of white roselle extract for 4 weeks can be increased by 6.6%. It can be learned that the white roselle extract can indeed increase the skin collagen.

Figure 11:
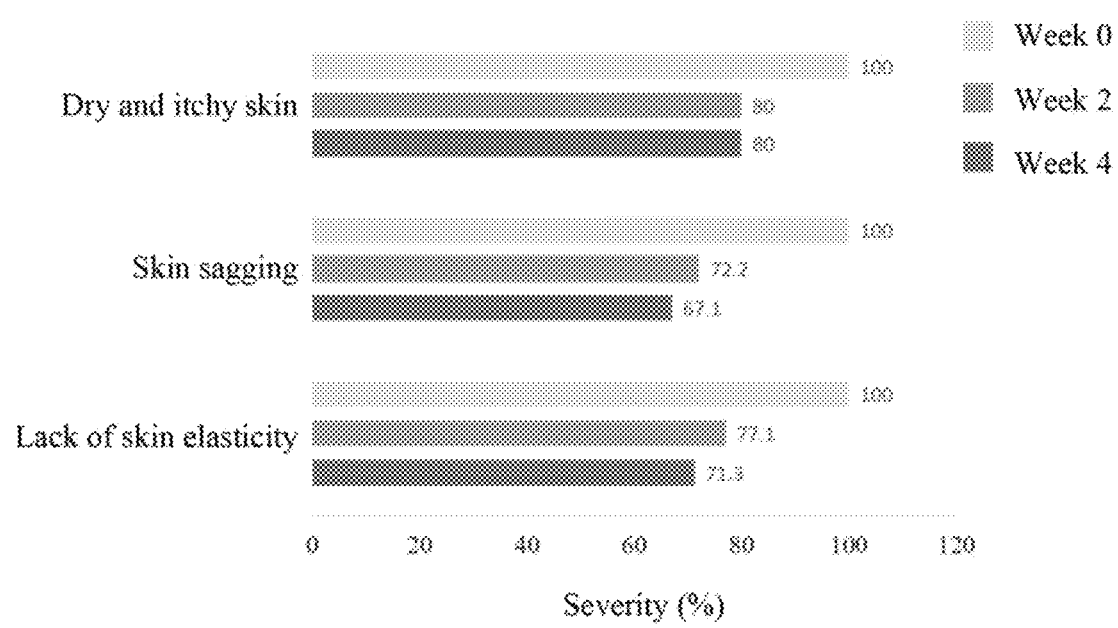
FIG. 11 is a graph showing percentages of self-assessment of skin condition questionnaire at week 0, week 2, and week 4 in some embodiments of the present invention.

6. The results of self-assessment of "skin condition questionnaire" of the subjects are shown in FIG. 11. A skin condition of nine subjects before drinking the white roselle extract drink (at week 0) by self-assessment was regarded as 100%. The skin conditions include dry and itchy skin, skin sagging, and lack of skin elasticity. For the subjects after drinking for 2 weeks and 4 weeks, severities of dry and itchy skin were 80.0% and 80.0% respectively; severities of skin sagging were 72.2% and 67.1% respectively; and severities of lack of skin elasticity were 77.1% and 71.3% respectively. In other words, compared with no drinking of the white roselle extract drink (week 0), the dry and itchy skin of the subjects after drinking the drink containing 1.5 mL of white roselle extract for 2 weeks can be reduced by 20.0%, and the dry and itchy skin of the subjects after drinking the drink containing 1.5 mL of white roselle extract for 4 weeks can be reduced by 20.0%; the skin sagging of the subjects after drinking the drink containing 1.5 mL of white roselle extract for 2 weeks can be reduced by 27.8%, and the skin sagging of the subjects after drinking the drink containing 1.5 mL of white roselle extract for 4 weeks can be reduced by 32.9%; and the lack of skin elasticity of the subjects after drinking the drink containing 1.5 mL of white roselle extract for 2 weeks can be reduced by 22.9%, and the lack of skin elasticity of the subjects after drinking the drink containing 1.5 mL of white roselle extract for 4 weeks can be reduced by 28.7%. Based on this, the subjects felt less dry and itchy skin, less skin sagging, and less lack of skin elasticity.

In conclusion, the white roselle extract of any embodiment can prepare a composition for enhancing skin moisture. In other words, the composition has the function of enhancing skin moisture. In some embodiments, in other words, the composition prepared from the white roselle extract also has one or more of the following functions: increasing an expression level of epidermal keratinocyte structure maintenance-related genes, increasing aquaporins, increasing an expression level of aquaporin genes, increasing ceramides, increasing ceramide generation-related genes, increasing hyaluronic acid secretion, and increasing an expression level of hyaluronic acid synthesis-related genes.

What is claimed is:

1. A method for enhancing skin moisture in a subject in need thereof, comprising administering to the subject a composition comprising a white roselle (*Hibiscus sabdariffa*cv.) extract, wherein the white roselle extract is obtained by lysing a cell wall of a white roselle calyx by ice crystals and extracting the lysed white roselle calyx with water.

2. The method according to claim 1, wherein the administering of said effective amount of the white roselle extract increases an expression level of epidermal keratinocyte structure maintenance-related genes to enhance skin moisture.

3. The method according to claim 1, wherein the administering of said effective amount of the white roselle extract increases aquaporins to enhance skin moisture.

4. The method according to claim 1, wherein the administering of said effective amount of the white roselle extract increase an expression level of aquaporin genes to enhance skin moisture.

5. The method according to claim 1, wherein the administering of said effective amount of the white roselle extract increases ceramides to enhance skin moisture.

6. The method according to claim 1, wherein the administering of said effective amount of the white roselle extract increases an expression level of ceramide generation-related genes to enhance skin moisture.

7. The method according to claim 1, wherein the administering of said effective amount of the white roselle extract increases hyaluronic acid secretion to enhance skin moisture.

8. The method according to claim 1, wherein the administering of said effective amount of the white roselle extract increases an expression level of hyaluronic acid synthesis-related genes to enhance skin moisture.

9. The method according to claim 1, wherein an effective dose of the white roselle extract is 1.5 mg/day.

10. The method according to claim 1, wherein the composition is a pharmaceutical composition, a food composition, a cosmetic composition, or a cosmeceutical composition.

* * * * *

SEQUENCE LISTING

```
<160> NUMBER OF SEQ ID NOS: 18

<210> SEQ ID NO 1
<211> LENGTH: 22
<212> TYPE: DNA
<213> ORGANISM: Artificial Sequence
<220> FEATURE:
<223> OTHER INFORMATION: TGM1

<400> SEQUENCE: 1
gatcgcatca cccttgagtt ac                                              22

<210> SEQ ID NO 2
<211> LENGTH: 19
<212> TYPE: DNA
<213> ORGANISM: Artificial Sequence
<220> FEATURE:
<223> OTHER INFORMATION: TGM1

<400> SEQUENCE: 2
gcaggttcag attctgccc                                                  19

<210> SEQ ID NO 3
<211> LENGTH: 21
<212> TYPE: DNA
<213> ORGANISM: Artificial Sequence
<220> FEATURE:
<223> OTHER INFORMATION: KRT1

<400> SEQUENCE: 3
agagtggacc aactgaagag t                                               21

<210> SEQ ID NO 4
<211> LENGTH: 21
<212> TYPE: DNA
<213> ORGANISM: Artificial Sequence
<220> FEATURE:
<223> OTHER INFORMATION: KRT1
```

-continued

<400> SEQUENCE: 4
attctctgca tttgtccgct t                                            21

<210> SEQ ID NO 5
<211> LENGTH: 22
<212> TYPE: DNA
<213> ORGANISM: Artificial Sequence
<220> FEATURE:
<223> OTHER INFORMATION: KRT10

<400> SEQUENCE: 5
tcctacttgg acaaagttcg gg                                           22

<210> SEQ ID NO 6
<211> LENGTH: 19
<212> TYPE: DNA
<213> ORGANISM: Artificial Sequence
<220> FEATURE:
<223> OTHER INFORMATION: KRT10

<400> SEQUENCE: 6
cccctgatgt gagttgcca                                               19

<210> SEQ ID NO 7
<211> LENGTH: 20
<212> TYPE: DNA
<213> ORGANISM: Artificial Sequence
<220> FEATURE:
<223> OTHER INFORMATION: KRT14

<400> SEQUENCE: 7
ttctgaacga gatgcgtgac                                              20

<210> SEQ ID NO 8
<211> LENGTH: 20
<212> TYPE: DNA
<213> ORGANISM: Artificial Sequence
<220> FEATURE:
<223> OTHER INFORMATION: KRT14

<400> SEQUENCE: 8
gcagctcaat ctccaggttc                                              20

<210> SEQ ID NO 9
<211> LENGTH: 19
<212> TYPE: DNA
<213> ORGANISM: Artificial Sequence
<220> FEATURE:
<223> OTHER INFORMATION: AQP3

<400> SEQUENCE: 9
ggggagatgc tccacatcc                                               19

<210> SEQ ID NO 10
<211> LENGTH: 21
<212> TYPE: DNA
<213> ORGANISM: Artificial Sequence
<220> FEATURE:
<223> OTHER INFORMATION: AQP3

<400> SEQUENCE: 10
aaaggccagg ttgatggtga g                                            21

<210> SEQ ID NO 11
<211> LENGTH: 20

```
<212> TYPE: DNA
<213> ORGANISM: Artificial Sequence
<220> FEATURE:
<223> OTHER INFORMATION: SMPD1

<400> SEQUENCE: 11
ctgactctcg ggttctctgg                                          20

<210> SEQ ID NO 12
<211> LENGTH: 20
<212> TYPE: DNA
<213> ORGANISM: Artificial Sequence
<220> FEATURE:
<223> OTHER INFORMATION: SMPD1

<400> SEQUENCE: 12
tccaccatgt catcctcaaa                                          20

<210> SEQ ID NO 13
<211> LENGTH: 20
<212> TYPE: DNA
<213> ORGANISM: Artificial Sequence
<220> FEATURE:
<223> OTHER INFORMATION: GBA

<400> SEQUENCE: 13
tccagttgca caacttcagc                                          20

<210> SEQ ID NO 14
<211> LENGTH: 20
<212> TYPE: DNA
<213> ORGANISM: Artificial Sequence
<220> FEATURE:
<223> OTHER INFORMATION: GBA

<400> SEQUENCE: 14
ttgtgctcag cataggcatc                                          20

<210> SEQ ID NO 15
<211> LENGTH: 23
<212> TYPE: DNA
<213> ORGANISM: Artificial Sequence
<220> FEATURE:
<223> OTHER INFORMATION: HAS2

<400> SEQUENCE: 15
aagaacaact tccacgaaaa ggg                                      23

<210> SEQ ID NO 16
<211> LENGTH: 20
<212> TYPE: DNA
<213> ORGANISM: Artificial Sequence
<220> FEATURE:
<223> OTHER INFORMATION: HAS2

<400> SEQUENCE: 16
ggctgggtca agcatagtgt                                          20

<210> SEQ ID NO 17
<211> LENGTH: 19
<212> TYPE: DNA
<213> ORGANISM: Artificial Sequence
<220> FEATURE:
<223> OTHER INFORMATION: HAS3

<400> SEQUENCE: 17
```

```
cgcagcaact tccatgagg                                              19

<210> SEQ ID NO 18
<211> LENGTH: 21
<212> TYPE: DNA
<213> ORGANISM: Artificial Sequence
<220> FEATURE:
<223> OTHER INFORMATION: HAS3

<400> SEQUENCE: 18
agtcgcacac ctggatgtag t                                           21
```